US00PP32485P2

(12) United States Plant Patent
Zwetsloot

(10) Patent No.: US PP32,485 P2
(45) Date of Patent: Nov. 17, 2020

(54) ***AGAPANTHUS* PLANT NAMED 'NOAGCAR'**

(50) Latin Name: *Agapanthus africanus*
Varietal Denomination: Noagcar

(71) Applicant: Jan Zwetsloot, Voorhout (NL)

(72) Inventor: Jan Zwetsloot, Voorhout (NL)

(73) Assignee: MARCO VAN NOORT BREEDING B.V., Warmond (NL)

( * ) Notice: Subject to any disclaimer, the term of this patent is extended or adjusted under 35 U.S.C. 154(b) by 0 days.

(21) Appl. No.: 16/873,123

(22) Filed: Feb. 5, 2020

(30) Foreign Application Priority Data

Sep. 11, 2019 (QZ) ..... PBR 20192216

(51) Int. Cl.
*A01H 5/02* (2018.01)
*A01H 6/56* (2018.01)

(52) U.S. Cl.
USPC ..... Plt./398
CPC ..... *A01H 6/56* (2018.05)

(58) Field of Classification Search
USPC ..... Plt./398
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Agapanthus* plant, 'Noagcar', that is characterized by its vigorous growth habit, its immature peduncles that are strongly tinged with black prior to the opening of the flowers, its flowers that are violet-blue in color with a dark longitudinal stripe, and its floriferous blooming habit.

2 Drawing Sheets

Botanical classification: *Agapanthus africanus.*
Varietal denomination: 'Noagcar'.

CROSS-REFERENCE TO A RELATED APPLICATION

This application claims priority to European Community Plant Variety Office (CPVO) Plant Breeder's Rights Application No. 2019/2216 filed on Sep. 11, 2019 under 35 U.S.C. 119(f), the entire contents of which is incorporated by reference herein.

BACKGROUND OF THE INVENTION

The present invention relates to a new and distinct cultivar of *Agapanthus africanus* and will be referred to hereafter by its cultivar name, 'Noagcar'. 'Noagcar' represents a new perennial grown for landscape use.

The new cultivar arose from an ongoing breeding program by the Inventor in Voorhout, The Netherlands. The objective of the breeding program was to develop a new cultivar of *Agapanthus* with a floriferous blooming habit and large flowers. The new cultivar arose from open pollination in August of 2012 of an unnamed and unpatented proprietary plant of *Agapanthus africanus*. The area contained numerous plants of unnamed and unpatented proprietary plants of *Agapanthus africanus* as a source of pollen; the exact male parent is therefore unknown. 'Noagcar' was selected as a single unique plant from the resulting seedlings in August of 2014.

Asexual propagation of the new cultivar was first accomplished by division in Voorhout, The Netherlands in September of 2016 under the direction of the Inventor. Asexual propagation by division and tissue culture using meristematic tissue has determined that the characteristics of this cultivar have been determined to be stable and are reproduced true to type in successive generations.

SUMMARY OF THE INVENTION

The following traits have been repeatedly observed and represent the characteristics of the new cultivar. The characteristics in combination distinguish 'Noagcar' as a distinct cultivar of *Agapanthus.*

1. 'Noagcar' exhibits a vigorous growth habit.
2. 'Noagcar' exhibits immature peduncles that are strongly tinged with black prior to the opening of the flowers.
3. 'Noagcar' exhibits flowers that are violet-blue in color with a dark longitudinal stripe.
4. 'Noagcar' exhibits a floriferous blooming habit.

The seed parent of 'Noagcar' differs from 'Noagcar' in having immature peduncles that are green in color and in producing less inflorescences when a young plant. 'Noagcar' can be most closely compared to the *Agapanthus* cultivars 'Senna' (U.S. Plant Pat. No. 19,972) and 'Back in Black' (not patented). 'Senna' and 'Back in Black' are both similar to 'Noagcar' in having peduncles that are black in color. 'Senna' differs from 'Noagcar' in having flowers that are slightly lighter and more purple in color, peduncles that retain their black coloration when the flowers open, and a shorter plant height. 'Back in Black' differs from 'Noagcar' in having flowers that are darker and much more purple in color, peduncles that retain their black coloration when the flowers open, and a shorter plant height.

BRIEF DESCRIPTION OF THE DRAWINGS

The accompanying colored photographs illustrate the overall appearance and distinct characteristics of the new *Agapanthus*. The photographs were taken of a 4-year-old plant of 'Noagcar' as grown outdoors in a 23-cm container in Warmond, The Netherlands.

The photograph in FIG. 1 provides a side view of a plant of 'Noagcar' in bloom.

Figure 1:
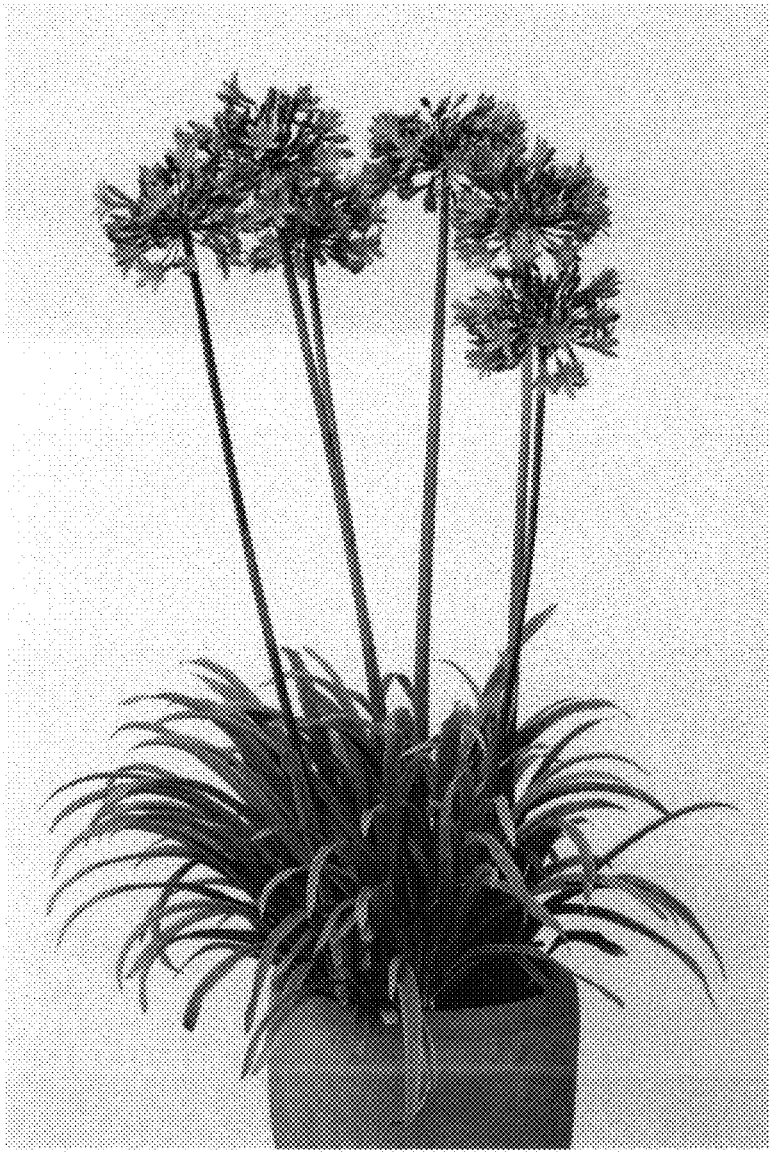
Figure 2:
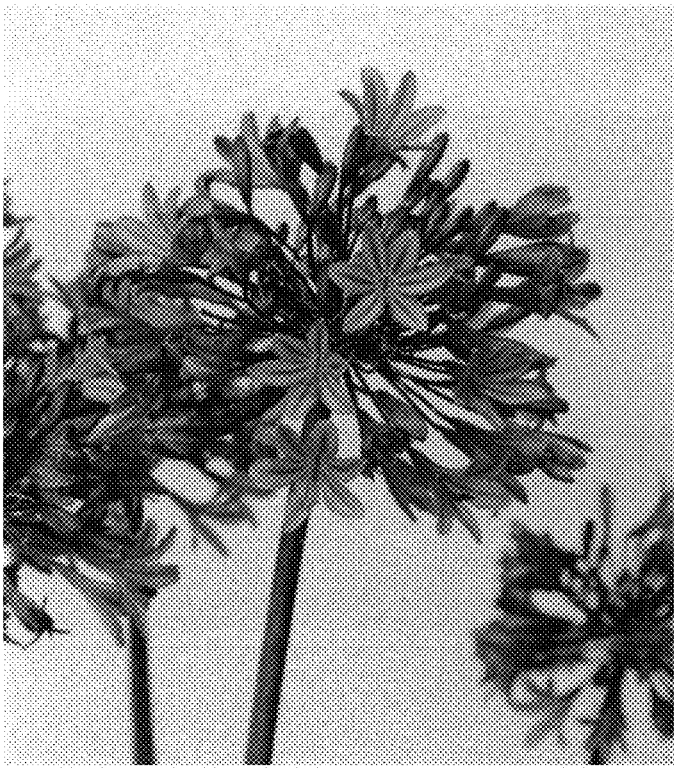

The photograph in FIG. 2 provides a close-up view of an inflorescence of 'Noagcar'.

Figure 3:
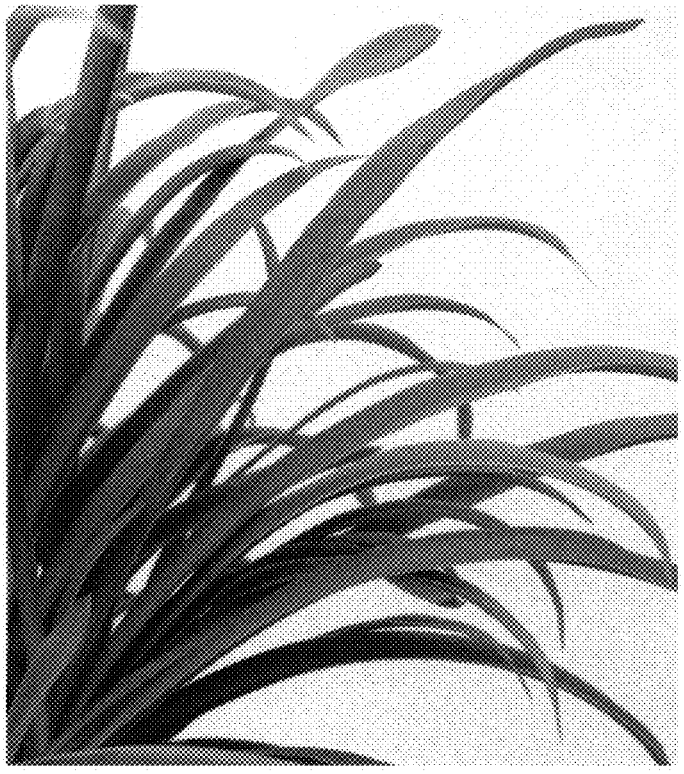

The photograph in FIG. 3 provides a close-up view of the foliage of 'Noagcar'.

The colors in the photographs are as close as possible with the photographic and printing technology utilized and color values cited in the detailed botanical description accurately describe the colors of the new *Agapanthus*

DETAILED BOTANICAL DESCRIPTION

The following is a detailed description of plants 4-years-in-age as grown outdoors in 23-cm circular containers in Warmond, The Netherlands. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Blooming period.*—6 weeks from mid-summer into fall in The Netherlands.

*Plant type*.—Evergreen perennial.

*Plant habit*.—Basal rosettes with upright inflorescences emerging from the rosette base.

*Height and spread*.—Average of 85 cm in height soil level to top of floral plane, average of 35.5 cm in height soil level to foliar plane, 35 cm in spread.

*Cold hardiness*.—Hardy at least to U.S.D.A. Zone 8.

*Diseases and pests*.—No resistance or susceptibility to diseases or pest has been observed.

*Root description*.—Thick and fleshy, 161C in color.

*Propagation*.—Tissue culture and division.

*Growth rate*.—Vigorous.

*Root development.*—4 to 5 weeks to initiate rooting, 10 to 12 weeks to produce a rooted cutting.

Foliage description:

*Leaf shape*.—Ligulate.

*Leaf division*.—Simple.

*Leaf base*.—Decurrent, broadly cuneate.

*Leaf arrangement*.—Basal rosettes, equitant.

*Leaf apex*.—Acute.

*Leaf aspect* (*curvature*).—Moderately carinate and moderately curved.

*Leaf venation*.—Parallel, upper surface; 137B, lower surface; 144B.

*Leaf margins*.—Entire.

*Leaf size*.—Up to 38.3 cm in length and up to 1.9 cm in width.

*Leaf surface*.—Smooth, glabrous, and dull on upper and lower surface.

*Leaf number*.—Average of 9 leaves per shoot (varying between 5 to 11).

*Leaf venation*.—Parallel.

*Leaf variegation*.—None.

*Leaf color*.—Young upper surface; 143A to 143C, young lower surface 144A to 144B, mature upper surface; 137A, venation 137B, mature lower surface 138A, venation 144B.

*Leaf attachment*.—Sessile to base.

Flower description:

*Inflorescence type*.—Dense umbel.

*Flower fragrance*.—Faint.

*Flower type*.—Single, campanulate, 40% of lower part fused, self-cleaning.

*Flower number.*—100 flowers per umbel, 600 per plant.

*Inflorescence size*.—Average of 11.8 cm in height and 15.1 cm in diameter.

*Inflorescence shape*.—Umbel, near globular.

*Flower size*.—3.4 cm in diameter, 2.9 cm in depth, 5 mm in diameter, tube; 1.3 cm in length and 5 mm in diameter.

*Lastingness of inflorescence*.—Average of 2 weeks.

*Flower aspect*.—Slightly nodding to upright.

*Peduncle*.—Strong, elliptic in cross-section, held at an average angle of 85° to horizontal, average of 70.1 cm in length and 9 to 11 mm in width, color between 143A and 146A with immature peduncles strongly tinged 203B. Surface is smooth and glabrous, matte and covered with a thin waxy layer 138B in color.

*Pedicels*.—Strong, average of 3.8 cm in length and 1.5 mm in width, held erect to outward (−40° to +90°), 138A in color and moderately tinged 203B, glabrous and slightly glaucous surface.

*Floral bracts*.—1 at the base of each pedicel, filiform in shape, average of 2.2 cm in length and 1 mm in width, 70C in color.

*Flower buds*.—Oblanceolate in shape, average of 2 cm in length and 6 mm in width, smooth and slightly velvety, matte surface, NN88A in color and a color between N89A and N92B towards the apex.

*Tepals*.—6, held in 2 rows (upper and lower), oblanceolate to slightly falcate in shape, broadly cuneate base, entire margins with low undulation, lower tepal 3.1 mm in length and 7 mm in width, upper tepal 3.4 mm in length and 9 mm in width, lower tepal apex bluntly acute, upper tepal apex narrowly obtuse, upper and lower surface smooth, glabrous and slightly velvety, and very slightly glossy, color: upper surface when opening; 92C, margins and tip 93C, central stripe 93A, lower surface when opening; N89D, apex and central stripe N89B, fully open upper surface; 93C, central stripe 93B, veins 93B, fully open lower surface; 92A and 93C, central stripe 93B, veins 93B, upper surface aging to N81A to N81B, lower surface aging to N80A, main veins a color between N92A and N92B, throat 93D in color, tube a color between 93A and 93B.

Reproductive organs:

*Gynoecium*.—1 pistil, average of 1.9 cm in length, stigma; club-shaped, 0.5 mm in length and diameter and 92D in color, style; 1.85 cm in length and 92B in color changing to 92D, ovary; 145C in color.

*Androecium*.—Stamens; 6, filaments; 1.5 cm in length, 92B in color fading to 92D, anthers; basifixed, oblong in shape, 2 mm in length, 0.8 mm in width, pollen; moderately abundant in quantity and 150B in color.

*Fruit/seed*.—Have not been observed.

It is claimed:

1. A new and distinct cultivar of *Agapanthus* plant named 'Noagcar' as herein illustrated and described.

* * * * *